(12) United States Patent
Noda (10) Patent No.: US 7,478,948 B2
(45) Date of Patent: Jan. 20, 2009

(54) BEARING AND X-RAY DIAGNOSTIC APPARATUS USING SAME

(75) Inventor: Koji Noda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/460,857

(22) Filed: Jul. 28, 2006

(65) Prior Publication Data
US 2007/0036273 A1  Feb. 15, 2007

(30) Foreign Application Priority Data
Aug. 9, 2005   (JP) ............................. 2005-230364

(51) Int. Cl.
*H05G 1/02* (2006.01)

(52) U.S. Cl. ................... 378/193; 378/204; 384/91; 384/621

(58) Field of Classification Search ......... 378/193–198, 378/204; 384/91, 114, 615–623
See application file for complete search history.

(56) References Cited

U.S. PATENT DOCUMENTS 3,456,114 A    7/1969   Gray ........................... 378/189
5,961,221 A *  10/1999  Kamimura ................... 384/447

FOREIGN PATENT DOCUMENTS

FR          930 286     1/1948
JP          4-812       1/1992

* cited by examiner

*Primary Examiner*—Courtney Thomas
(74) *Attorney, Agent, or Firm*—Oblon, Spivak, McClelland, Maier & Neustadt, P.C.

(57) ABSTRACT

A rotary mechanism uses a rolling element, an outer-ring housing member and an inner-ring housing member. The outer-ring housing member or the inner-ring housing member is divided thicknesswise into two parts, to have a gap at between the two-divided parts of the housing member. Due to this, slide resistance can be caused by deforming the rolling element received in the outer-ring and inner-ring housing members.

12 Claims, 7 Drawing Sheets

BEARING AND X-RAY DIAGNOSTIC APPARATUS USING SAME

BACKGROUND OF THE INVENTION

1. Field of the Invention

This invention relates to a bearing and a medical X-ray diagnostic apparatus using the same. More particularly, the invention relates to an X-ray diagnostic apparatus having a support mechanism rotatably structured with supporting a C-formed arm oppositely provided with an X-ray tube and an imager.

2. Description of the Related Art

In the X-ray diagnosis concerning the region including the circulatory system, particularly the heart, it is conventionally desired to conduct a stereoscopic observation by taking X-ray images in a multiplicity of directions. For this reason, there is an X-ray diagnostic apparatus having a C-formed arm (hereinafter, referred to as a C-arm) having, at one end, an X-ray tube and, at the other end, an imager including an image intensifier (I. I.) and a television camera unit (TV camera) wherein the C-arm is allowed to rotate or slide in a C-form direction.

Figure 1:
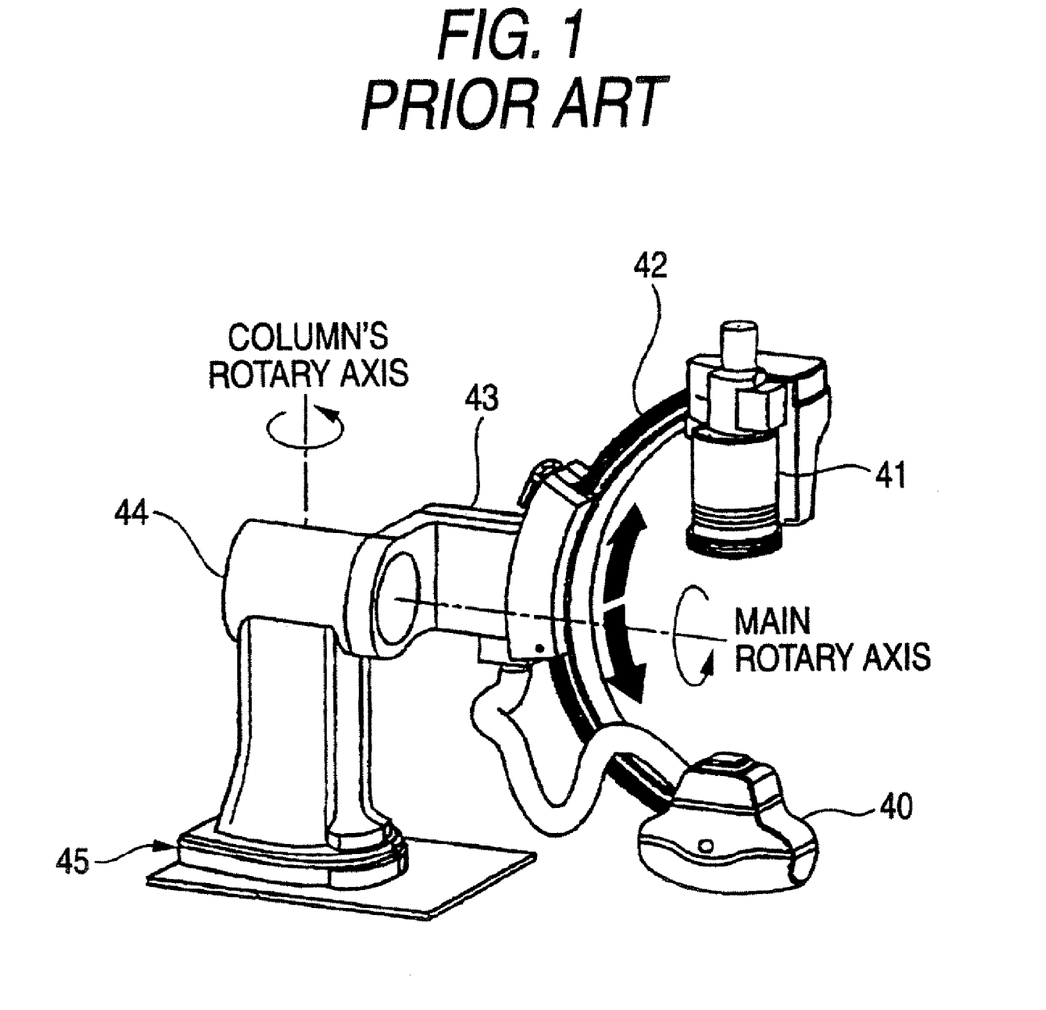
FIG. 1 is a view showing an example of the existing fix-type X-ray diagnostic apparatus.

The X-ray diagnostic apparatuses, having such C-arms, includes, say, a fix-type X-ray diagnostic apparatus (JP-A-2001-137222). FIG. 1 is a perspective view showing a fix-type X-ray diagnostic apparatus. As shown in FIG. 1, the fix-type X-ray diagnostic apparatus is constructed with a stand 45, a column 44 rotatably supported on the stand 45 about a column's rotary axis vertical to the floor, a C-arm 42 having an X-ray tube 40 and an imager 41, and an arm support 43 rotatably supported on the column 44 about a main rotary axis orthogonal to the column's rotary axis and holding the C-arm 42 slidable along the C-form. In this case, the support mechanism structured for horizontal rotation refers to the column 44.

Figure 2:
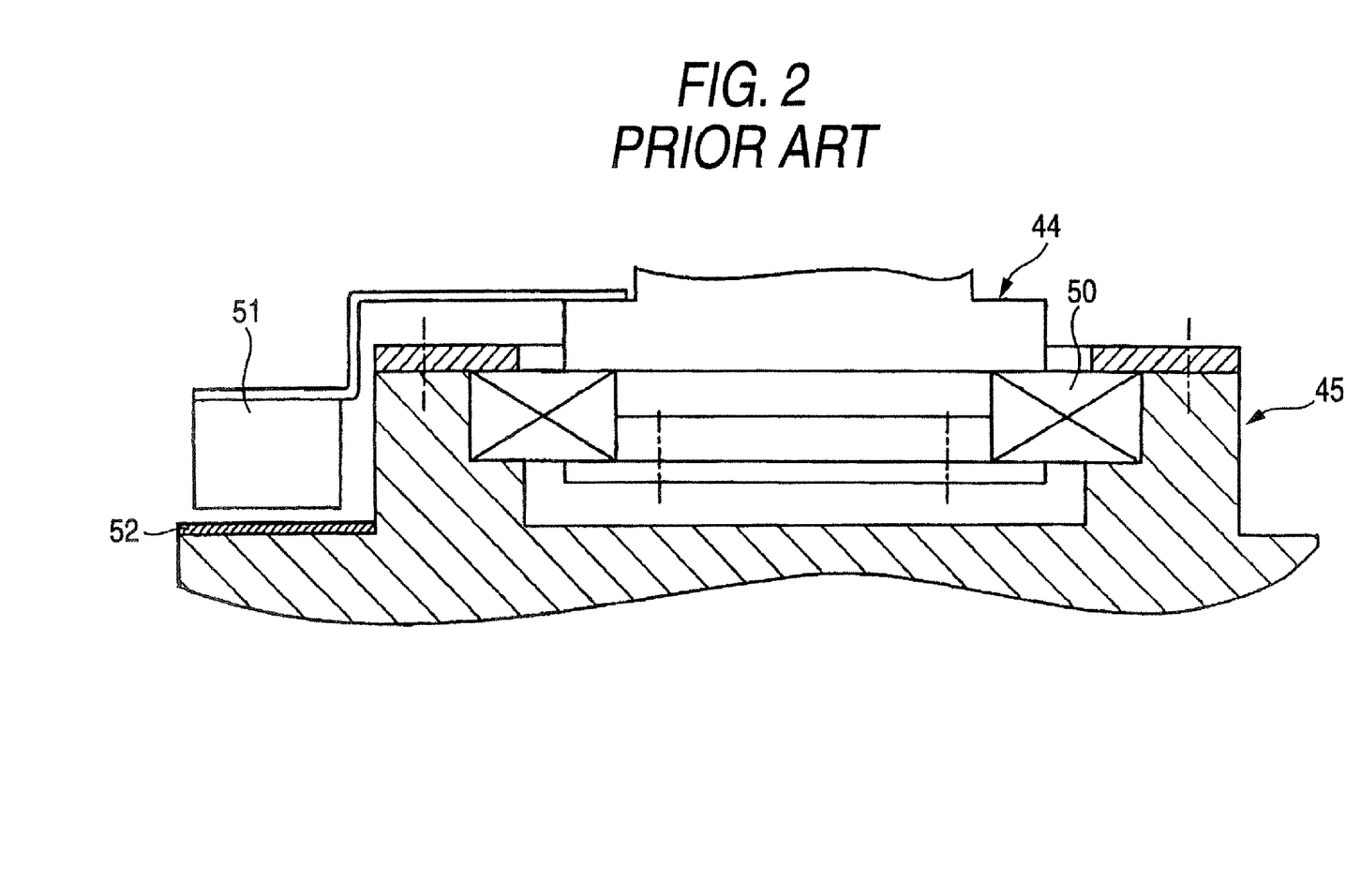
FIG. 2 is a sectional view showing the periphery of a rotary mechanism of the existing fix-type X-ray diagnostic apparatus.

FIG. 2 shows a sectional view of the rotary mechanism supporting the column 44 horizontally rotatably. As shown in FIG. 2, the column 44 is supported on the stand 45 through a bearing 50.

However, the bearing 50 cannot support the column in a manner not to rotate due to the inertia force caused upon sliding the C-arm 42 or upon rotating it about the main rotary axis.

Accordingly, there is a need to provide a rotary support mechanism in order to prevent the column from rotating due to the inertia force caused by movement of the C-arm. For example, it is a practice to employ an electromagnetic brake having an electromagnet 51 on the column 44 side so that the column 44 can be fixed on the stand 45 by energizing the electromagnet 51 and attract the electromagnet 51 to the attractive member 52 on the stand 45 side. Besides such an electromagnetic brake mechanism, there are cases to employ a structure having a self-lock mechanism in the speed reducer.

Namely, the mechanism is complicated because of the necessity of a rotary support mechanism for supporting the column not to rotate in addition to the rotary mechanism supporting the column 44 for horizontal rotation. Meanwhile, in order to secure the torque for holding the column not to rotate, there is a need to use a large-sized electromagnet or attaching an electromagnet in a position greatly distant from the column's rotary axis. Accordingly, the periphery of the rotary mechanism is inevitably size-increased because of providing a rotary support mechanism for supporting the column not to rotate. Meanwhile, it also constitute a factor to size-increase the apparatus overall besides the periphery of the rotary mechanism.

SUMMARY OF THE INVENTION

It is an object of the present invention to provide a bearing capable of easily constituting a rotary support mechanism for holding freely from rotation and an X-ray diagnostic apparatus using the bearing.

A first aspect of the invention is a bearing comprising a rolling element, an outer-ring housing member and an inner-ring housing member. The outer-ring housing member has, at an inner peripheral side, a raceway along which the rolling element is to roll, wherein the raceway and a part of the rolling element are in contact. The inner-ring housing member is smaller in diameter than the outer-ring housing member and having, at an outer peripheral side, a raceway along which the rolling element is held and allowed to roll. The raceway is opposed to the raceway of the outer-ring housing member and in contact with a part of the rolling element. The raceways of the outer-ring and inner-ring housing members form a container receiving the rolling element therein. At least one of the outer-ring housing member and the inner-ring housing member is divided thicknesswise into two parts, to have a gap between the two-divided parts of the housing member.

According to the first aspect, at least one of the outer-ring and the inner-ring housing members is divided thicknesswise into two parts, to have a gap between the two-divided parts of the housing member. Due to this, slide resistance can be caused by deforming the rolling element received in the outer-ring or the inner-ring housing member.

A second aspect of the invention is an X-ray diagnostic apparatus having a support mechanism structured for rotation. The support mechanism holds an arm provided with an X-ray tube at one end and an imager at the other end. The rotary mechanism for rotation includes a bearing. The bearing includes a rolling element, an outer-ring housing member and an inner-ring housing member. The outer-ring and inner-ring housing members are to slide through the rolling element, and form a container receiving the rolling element. The rolling element is received deformed in the container.

According to the second aspect, the rolling element, of the bearing used in the rotary mechanism, is to be deformed by the container for the rolling element, to cause a slide resistance in the rotational direction. Accordingly, the rotary mechanism can realize the function of a rotary support mechanism for holding freely from rotating.

Meanwhile, a third aspect of the invention is an X-ray diagnostic apparatus comprising a support mechanism structured for rotation. The support mechanism supports an arm provided with an X-ray tube at one end and an imager at the other end. A rotary mechanism for rotation includes a bearing, an outer-ring holder and an inner-ring holder. The bearing includes a rolling element, an outer-ring housing member and an inner-ring housing member. The outer-ring and inner-ring housing members are to slide through the rolling element. The outer-ring holder has a grooved opening supporting the outer-ring housing member of the bearing. The inner-ring holder has a grooved opening supporting the inner-ring housing member of the bearing. At least one of the outer-ring and inner-ring housing members is vertically divided into two parts. The grooved opening of the outer-ring holder or the inner-ring holder at a side of the two-divided housing member has a dimension smaller than a vertical dimension of the two-divided housing member when the rolling element is in contact with the two-divided housing member.

According to the third aspect, the holder supporting the bearing has a dimension smaller than the vertical dimension of the two-divided housing member. When the bearing is held, the rolling element of the bearing deforms to cause a slide resistance in the rotating direction. Accordingly, the rotary mechanism can realize the function of a rotary support mechanism for holding freely from rotation, thus size-reducing the periphery of the rotary mechanism of the X-ray diagnostic apparatus.

DETAILED DESCRIPTION OF THE PREFERRED EMBODIMENTS

Figure 3:
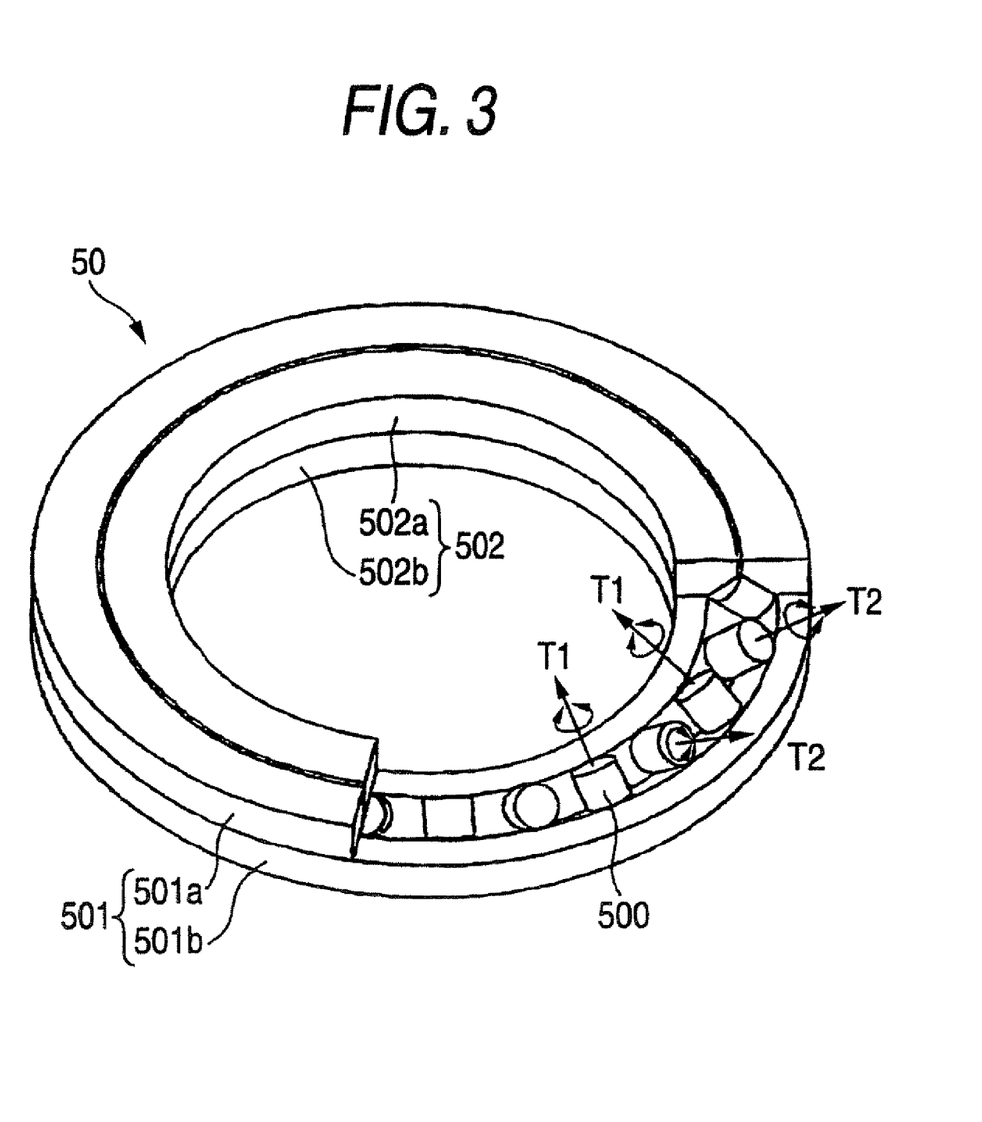
FIG. 3 is a perspective view showing a manner of rotation of a rolling element in a bearing according to an embodiment.

At first, a bearing according to the invention is explained. Explanation is by use of FIGS. 3 and 4. FIG. 3 is a view showing an embodiment of a bearing according to the invention. In FIG. 3, a cross roller bearing is illustrated as one example.

As shown in FIG. 3, a bearing 50 is made up with a plurality of rolling elements 50 that are rollers in form, an outer-ring housing member 501 and an inner-ring housing member 502. The outer-ring and inner ring housing members 501, 502 are formed in ring forms, which respectively are divided vertically (thicknesswise) into two parts, thus being structured with outer-ring housing members 501a, 501b and inner-ring housing members 502a, 502b. In FIG. 3, the outer-ring housing member 501a and the inner-ring housing member 502a are shown by omitting a part thereof, in order to show the rolling elements 500. The rolling elements 500 are arranged with the roller-axis direction changed alternately. For example, those are provided such that one is in a direction of T1 while the adjacent one is in a direction of T2, as shown in FIG. 3. The rolling element 500 is to roll by its rotation about the roller axis. Due to this, the outer-ring and inner-ring housing members 501, 502 are allowed to slide through the rolling elements 500.

Figure 4:
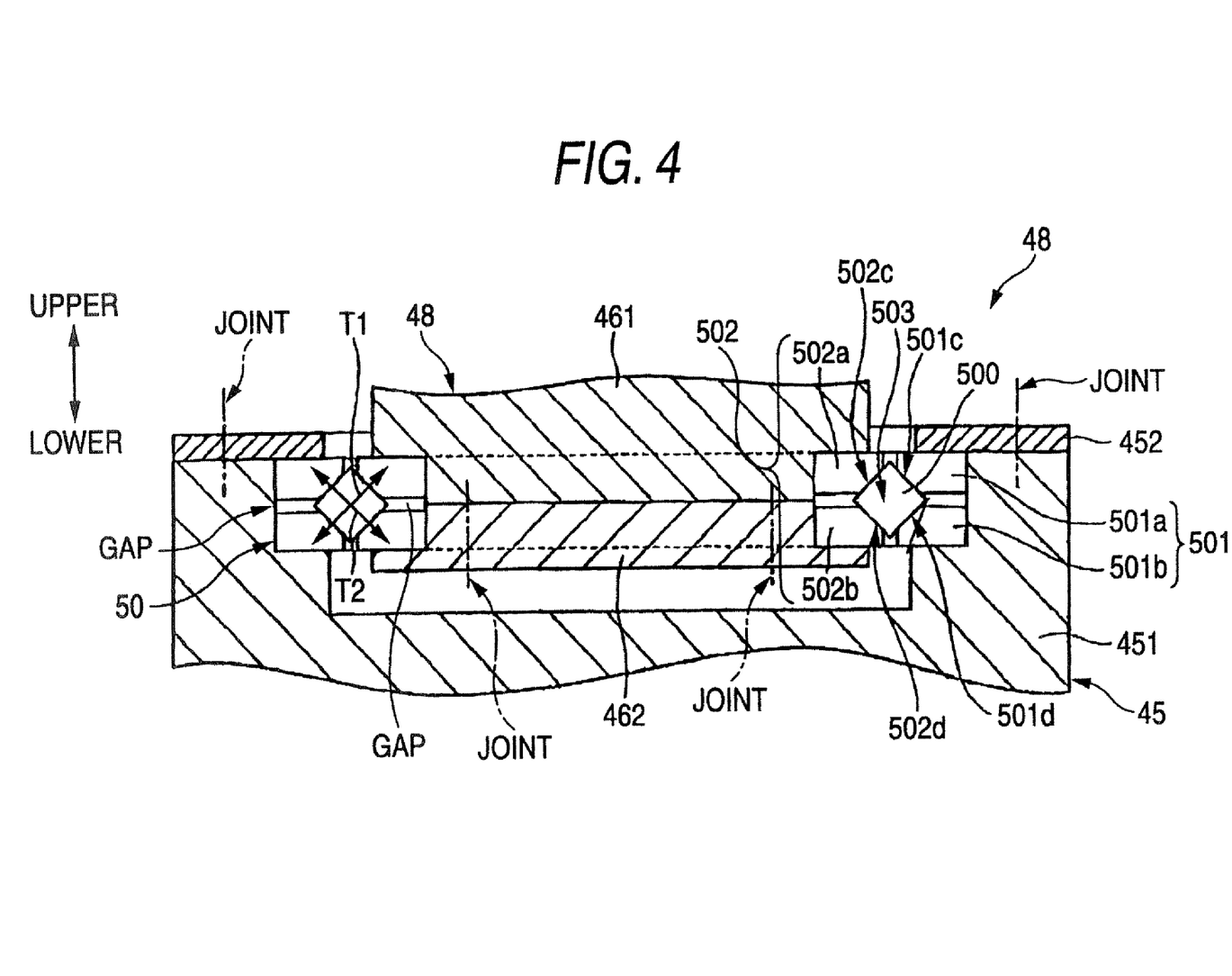
FIG. 4 is a sectional view showing a structure of a rotary mechanism according to the present invention.

FIG. 4 shows a section of the bearing in this embodiment. In FIG. 4, the outer-ring housing member 501 is held by a bearing receiver 451 cylindrically formed and a bearing support member 452 while the inner-ring housing member 502 is held by a bearing receiver 461 and a bearing support member 462.

As shown in FIG. 4, a raceway 501c is formed in the inner peripheral side of the outer-ring housing member 501a such that it contacts with the rolling elements 500 and the roller elements 500 are to roll while a raceway 501d is formed in the inner peripheral side of the outer-ring housing member 501b such that it contacts with the rolling elements 500 and the roller elements 500 are to roll. The raceway 501c and the raceway 501d are formed orthogonal in section, as shown in FIG. 4. Meanwhile, a raceway 502c is formed in the outer peripheral side of the inner-ring housing member 502a such that it contacts with the rolling elements 500 and the roller elements 500 are to roll while a raceway 502d is formed in the outer peripheral side of the inner-ring housing member 502b such that it contacts with the rolling elements 500 and the roller elements 500 are to roll. The raceway 502c and the raceway 502d are formed orthogonal in section, as shown in FIG. 4. The raceways 501c and 502d and the raceways 502c and 501d are respectively formed opposite. The raceways 501c, 501d, 502c, 502d form a container 503 (shown overlapped with the rolling element 500, in the figure), to receive the rolling elements 500 in the container 503. The rolling elements 500 are received in the container 503, with their roller-axis directions changed alternately as T1 and T2 (see FIG. 3). The container 503 is filled therein with lubricant, such as grease.

The outer-ring housing members 501a, 501b and the inner-ring housing members 502a, 502b have gaps at their splits.

Here, by setting the thickness dimension of the retainer formed by the bearing receiver 451 and bearing support member 452 and by the bearing receiver 461 and bearing support member 462 smaller than the thickness dimension of the outer-ring housing member 501 and the inner housing member 502, the bearing 50 is reduced of its gap and assembled as shown in FIG. 4. Thereupon, the container 503 is reduced in dimension, i.e. the container 503 is provided smaller in dimension relative to the rolling element 500. As a result, the rolling elements 500 are deformed to cause a slide resistance.

By thus using the bearing of the embodiment in the rotary mechanism in a manner to cause a slide resistance, rotation is facilitated wherein holding can be made not to rotate due to a slide resistance.

Although the explanation was on the example with the cross roller bearing using the roller-formed rolling elements 500 in the bearing 50, the rolling elements may be balls. Meanwhile, any one of the outer-ring and inner-ring housing members 501, 502 may be structured divided vertically into two parts. By providing a dimensional difference between the rolling element 500 and the container 503 by such a divisional side of housing member, the rolling element 500 may be in an oversize dimension as compared to the container 503, thereby elastically deforming the rolling elements 500 and causing a slide resistance.

Figure 5:
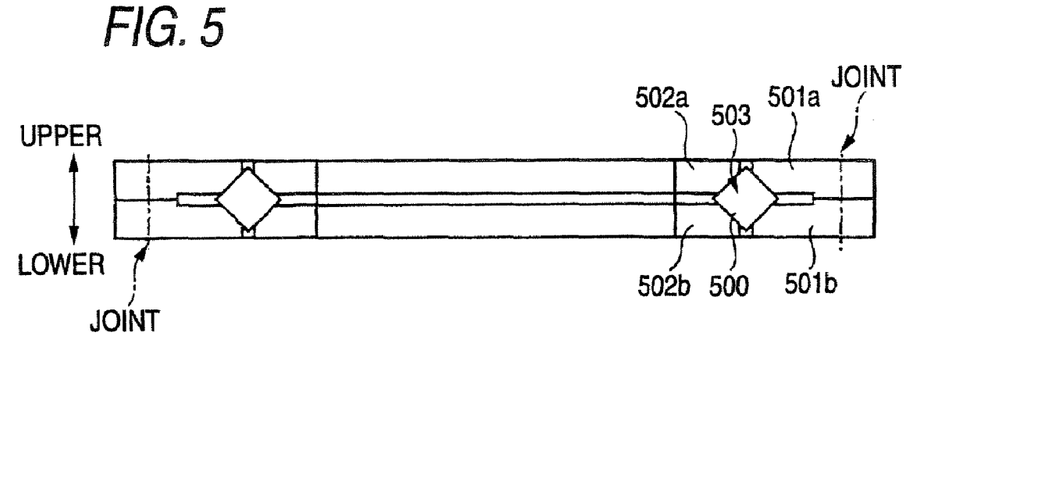
FIG. 5 is a sectional view showing an example of a structure of a bearing according to the invention.

Meanwhile, by vertically dividing at least either one of the outer-ring housing member 501 or the inner-ring housing member 502 and tightening the divided housings together by means of tightening members as shown in FIG. 5, the container 503 can be reduced in size as compared to the rolling element 500. FIG. 5 shows, as one example, a bearing tightened by the tightening members, at the joints of the outer-ring housing member 501, that are shown at one-dot chain lines. This can easily make the structure to hold the bearing for the apparatus.

While referring to the drawings, explanation is now made in detail on one embodiment of an X-ray diagnostic apparatus using the bearing according to the invention. In the figures, like reference numerals are attached to like constituent elements.

X-ray Diagnostic Apparatus Construction

Figure 6:
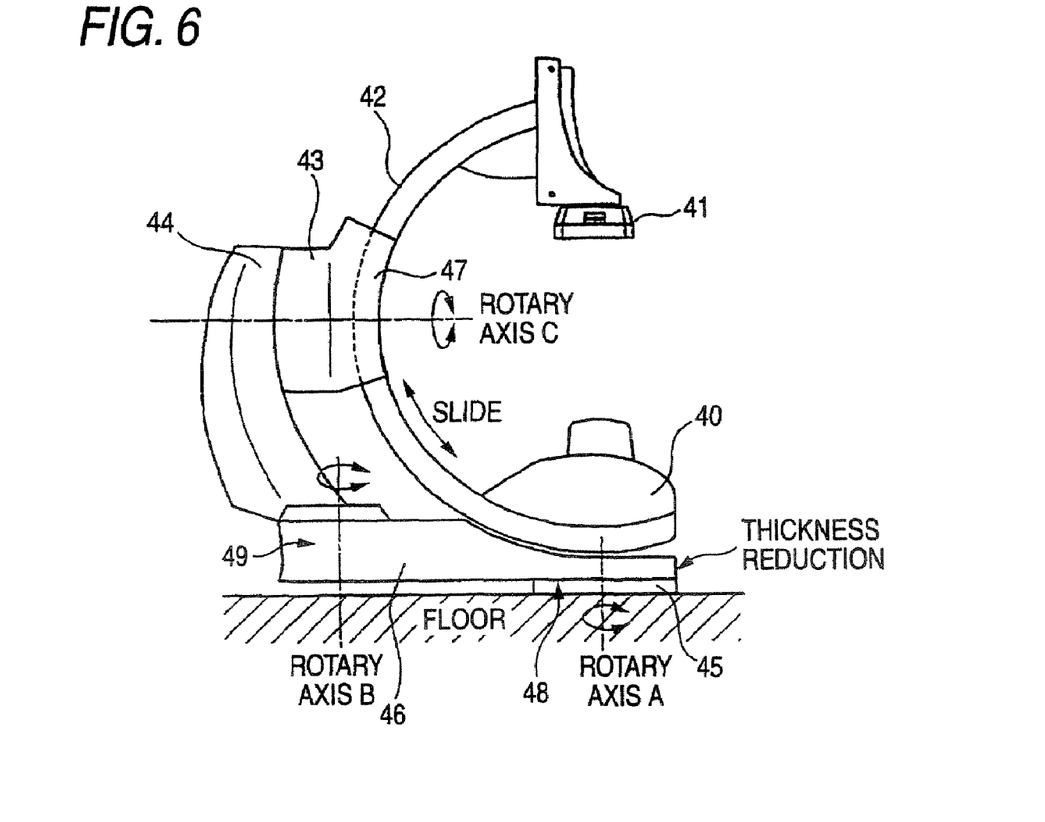
FIG. 6 is an exterior side view showing a structure of a fix-type X-ray diagnostic apparatus in the present embodiment.

FIG. 6 is an exterior side view showing a construction of a fix-type X-ray diagnostic apparatus in the present embodiment. As shown in FIG. 6, the X-ray diagnostic apparatus in this embodiment includes a stand 45, a floor arm (support mechanism) 46, a column (support mechanism) 44, an arm support 43, and a C-form arm (hereinafter, referred to as a C-arm) 42 having an X-ray tube 40 and an imager 41.

The stand 45 is fixed on a floor, say, by fixing means, not shown. The stand 45 bears thereon a floor arm 46 through a rotary mechanism 48.

The floor arm 46 is structured supported on the stand 45 so that it can horizontally rotate about a rotary axis A vertical to the floor. The floor arm 46 is in an arm form having one end supported on the stand 45, as noted above, and extending horizontally therefrom. The floor arm 46 has the other end where the column 44 is supported through a rotary mechanism 49, referred later. Meanwhile, the floor arm 46 has, at around the rotary axis A, an upper surface formed reduced in thickness in order to avoid the physical interference with the C-arm.

The invention can be applied to a part of a rotary mechanism that the components, connected rotatable relative to each other, are to rotate in a direction nearly parallel with the floor surface (i.e. rotation plane is given by a plane parallel with the floor surface). In the present embodiment, it can be suitably applied to at least either one of the rotary mechanism 48 or the rotary mechanism 49.

The column 44 is structured supported on the upper surface of the floor arm 46 and horizontally rotatable about a rotary axis B vertical to the floor. The column 44 is in a pillar form extending upward from the floor-arm 46 side, at the upper side of which is held an arm support 43 that supports the C-arm 42 through a rotary mechanism, not shown.

The arm support 43 is structured supported at the upper side of the column 44 and rotatable about a rotary axis C orthogonal to the rotary axis B. Meanwhile, at a tip of the rotary axis C, a C-arm driver 47 is provided to slide the C-arm 42 along its C-form.

The C-arm 42 has one end provided with an X-ray tube 40 and the other end provided with the imager 40 including X-ray detecting means. The X-ray detecting means herein is structured as a flat panel detector (FPD). The FPD roughly includes two types. One is a direct conversion type that uses a charge, caused upon absorbing an X-ray by a photoconductor, directly as a signal. The other is an indirect conversion type that the light, caused by once absorbing an X-ray in a phosphor, is converted by a photodiode into a charge thus obtain a signal. Any of those is applicable for the present embodiment. The FPD is thin and light-weighted. In the X-ray diagnostic apparatus having many rotary mechanisms and for realizing complicated (unique) movement as in the invention, the rotary mechanisms can be relieved of the force applied thereto during moving the X-ray detecting means by rotating the C-arm 42. Accordingly, the X-ray detecting means can be moved correctly to an image-taking position and stopped at the optimal image-taking position by suppressing the inertia force applied upon stoppage at an image-taking position. For such a reason, a flat panel detector is meaningfully employed for the X-ray detecting means.

Meanwhile, although not shown, there are provided a floor-arm driver for rotating the floor arm 46 horizontally, a column driver for rotating the column 44 horizontally, and an arm-support driver for rotating the arm support 43.

The X-ray diagnostic apparatus constructed as above allows for taking an X-ray image in a variety of directions by placing a subject between the X-ray tube 40 and the imager 41 and then operating the drivers.

Here, explanation is made on the structure of the rotary mechanism 48 by using FIG. 4. FIG. 4 is a sectional view, showing a structure of the rotary mechanism 48, taken on the plane including the rotary axis A.

As shown in FIG. 4, the rotary mechanism 48 includes a bearing 50, a bearing receiver 451 formed cylindrical on the stand 45, a bearing support member 452, a bearing receiver 461 formed in a flanged-shaft form with the floor arm 46, and a bearing support member 462.

Figure 7A:
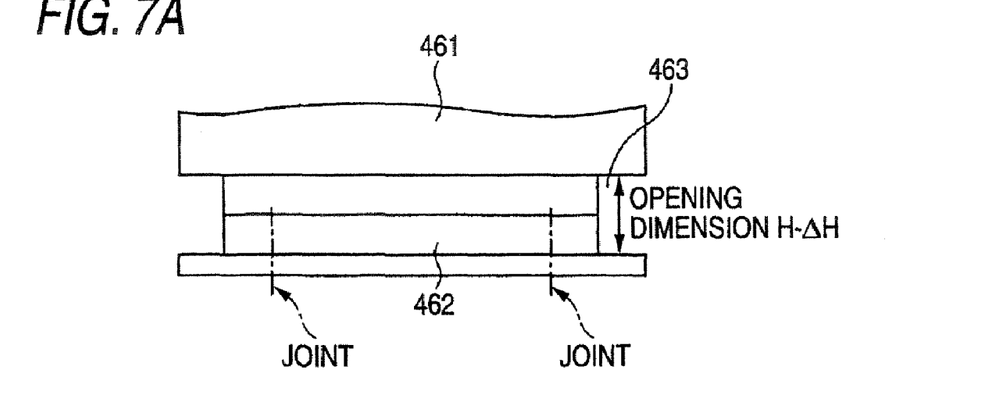
FIG. 7A is a view showing a dimension of an opening in the inner-ring holder.
Figure 7B:
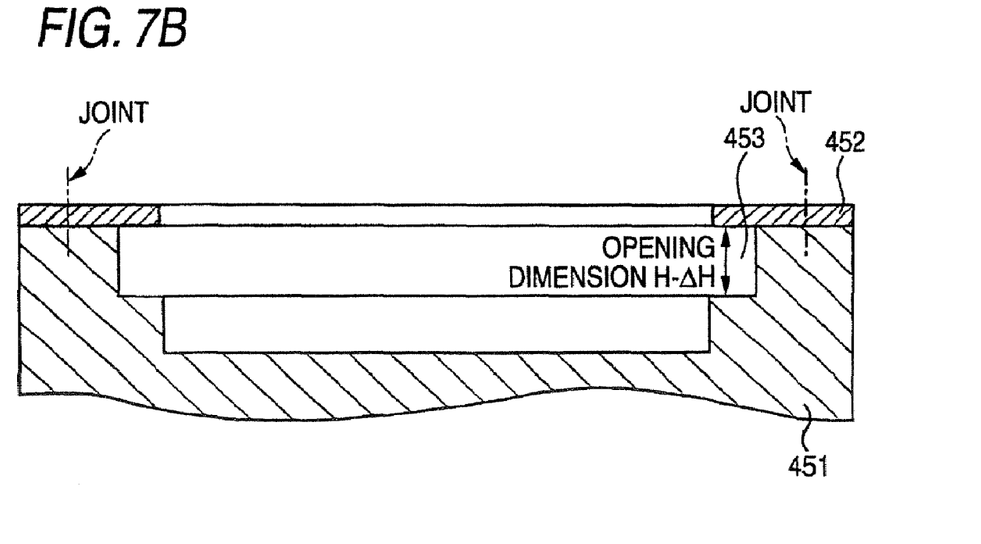
FIG. 7B is a view showing a dimension of an opening in the outer-ring holder.
Figure 7C:
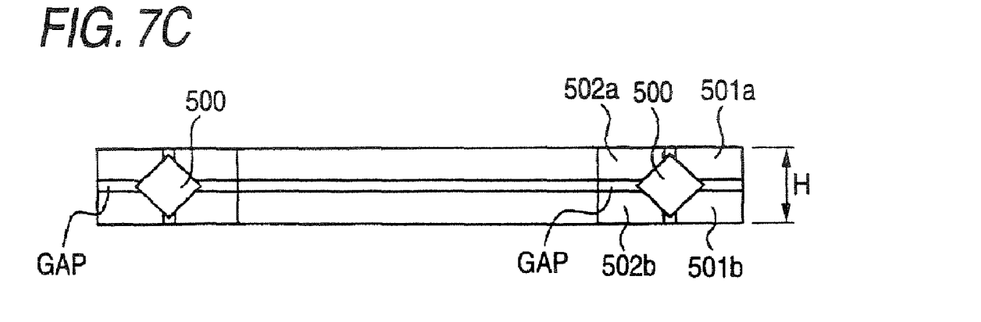
FIG. 7C is a view showing a vertical dimension of outer-ring and inner-ring housing members.

Meanwhile, as shown in FIG. 7C, when the outer-ring and inner-ring housing members 501, 502 are placed in a state contacted with the rolling element 500, the outer-ring housing members 501a, 501b has a gap at a split thereof while the inner-ring housing members 502a, 502b has a gap at a split thereof. In the state the outer-ring and inner-ring housing members 501, 502 are in a contacted state with the rolling element 500, the outer-ring housing member 501 and the inner-ring housing member 502 have a vertical dimension of H.

As shown in FIG. 7B, the bearing receiver 451 and the bearing support member 452 are tightened together at a plurality of joints (shown by one-dot chain lines, in the figure) by means of tightening members, e.g. bolts, not shown, thus forming an outer-ring support 453 having a grooved opening. The outer-ring support 453 holds the outer-ring housing member 501 of the bearing 50. The opening of the outer-ring support 453 has a dimension of H−ΔH.

As shown in FIG. 7A, the bearing receiver 461 and the bearing support member 462 are tightened together at a plurality of joints by tightening members, e.g. bolts, not shown, thus forming an inner-ring support 463 having a grooved opening. The inner-ring support 463 holds the inner-ring housing member 502 of the bearing 50. The opening of the inner-ring support 463 has a dimension of H−ΔH.

Namely, in the X-ray diagnostic apparatus of this embodiment, the outer-ring and the inner-ring supports 453, 463 have respective openings ΔH smaller in dimension relative to the thickness dimensions of the outer-ring and inner ring housing members 501, 502, respectively. Accordingly, by tightening the outer-ring housing member 501 and the inner-ring housing member 502 by the tightening members in a manner held by the outer-ring support 453 and the inner-ring support 463 respectively, the outer-ring housing member 501 and the inner-ring housing member 502 have a vertical dimension of H−ΔH conforming to the dimension of the grooved opening. Because this makes the container 503 ΔH smaller vertically, the rolling element 500 is ΔH oversize in dimension as compared to the container 503. Namely, when the outer-ring and inner-ring housing members 501, 502 are respectively held by the outer-ring and inner-ring supports 453, 463, the container 503 is ΔH smaller than the rolling element 500. As a result, the rolling element 500 deforms. In this case, ΔH is provided within the elasticity limit of the rolling element 500, i.e. within the range the rolling element 500 is to elastically deform. Meanwhile, naturally, the respective gaps at the splits of between the outer-ring housing members 501a, 501b and between the inner-ring housing members 502a, 502b are given greater than H.

By deforming the rolling elements 500, slide resistance can be caused in the rotating direction. For example, by providing ΔH of nearly 10 μm to a bearing using roller-type rolling elements having an inner diameter 400 mm, an outer diameter 500 mm and a thickness 40 mm, slide resistance can be caused at nearly 18 N·m. By such a slide resistance, the floor arm 46 can be held not to rotate due to the movement of the C-arm, for example. Meanwhile, slide resistance is given a resistance force not to raise a trouble in a rotation due to the floor-arm driver.

As discussed so far, slide resistance can be caused in the rotating direction in the bearing by the above structure. Namely, the use of a bearing as described makes it possible to realize the function of a rotary mechanism and the function of a rotation-free support mechanism that holds the floor arm 46 not to rotate. Therefore, there is eliminated the need of a rotation-free support mechanism as described in Background Art, thus making compact the periphery of the rotary mechanism 48.

Meanwhile, the rotary mechanism 48 can be made compact vertically due to the eliminated need of a rotation-free support mechanism. Accordingly, the floor arm 46 can be formed with a reduced thickness in a region near the rotary axis A as explained with FIG. 6. When the isocenter (radiation center) is positioned above the rotary axis A of the floor arm 46, it is possible to avoid the physical interference with the C-arm. Accordingly, the C-arm can be provided in a lower position relative to the floor. Because this allows a subject to be placed in a low position, operation is easy to perform on the subject when performing an operation. Meanwhile, because the rotary mechanism 48 can be made compact radially, apparatus installation space can be narrowed. The operator can easily perform an operation because allowed to access a subject closer.

Meanwhile, the rotary mechanism 49 can be similarly structured.

Figure 8:
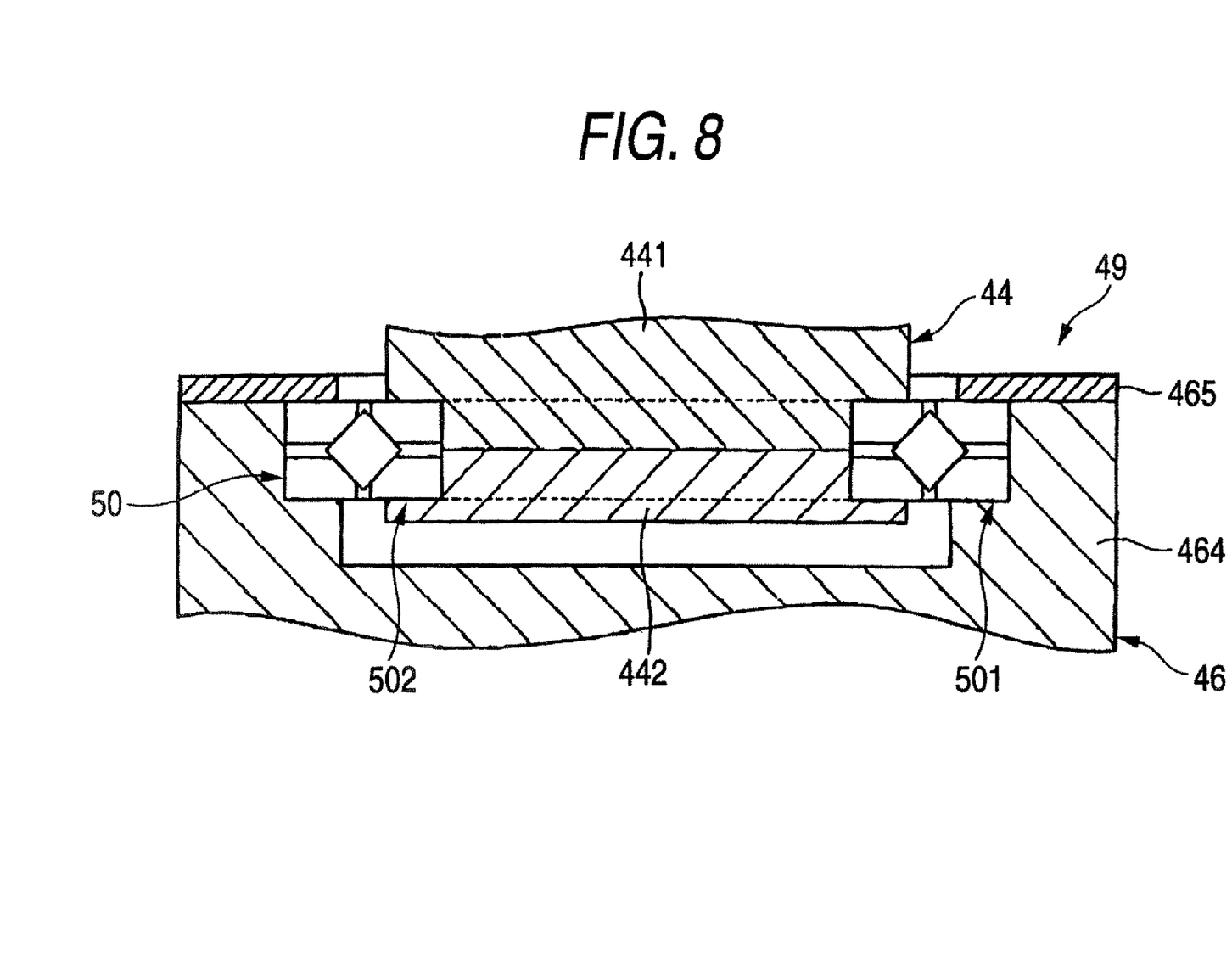
FIG. 8 is a sectional view showing a structure of the rotary mechanism in a position different from FIG. 4.

Here, the structure of the rotary mechanism 49 is explained by using FIG. 8. FIG. 8 is a view showing a structure of the rotary mechanism 49, which is a sectional view taken on a plane including the FIG. 6 rotary axis B.

As shown in FIG. 8, the rotary mechanism 49 includes a bearing 50, a bearing receiver 464 formed cylindrical in the floor arm 46, a bearing support member 465, a bearing receiver 441 formed in a flanged-shaft form with the column 44, and a bearing support member 442. Incidentally, the bearing 50 is held by the bearing receiver 464 in the floor arm 46, the bearing support member 465, the bearing receiver 441 in the column 44, and the bearing support member 442, similarly to the holding by means of the stand 45 and floor arm 46.

Due to this, the bearing 50 is allowed to cause a slide resistance in the rotational direction. Namely, the use of a bearing as described makes it possible to realize the function of a rotary mechanism and the function of a rotation-free support mechanism that holds the column 44 not to rotate. Therefore, there is eliminated the need of a rotation-free support mechanism, thus making it possible to make compact the periphery of the rotary mechanism 49.

Meanwhile, because the rotary mechanism 49 can be also made compact radially, the floor arm 46 can be reduced in the distance of from the rotary axis A. Namely, the rotation radius of the floor arm 46 is reduced with a result that installation space can be reduced.

Incidentally, although the rotary mechanism for horizontal rotation was exemplified, the rotary mechanism may structurally have its rotary axis inclining relative to the horizontal.

What is claimed is:

1. An X-ray diagnostic apparatus comprising:
 a support mechanism that supports an arm provided with an X-ray tube at one end and an imager at the other end; and
 a rotary mechanism that makes the support mechanism rotatable;
 the rotary mechanism including a bearing, an outer-ring holder and an inner-ring holder;
 the bearing including a rolling element, an outer-ring housing member and an inner-ring housing member, the outer-ring and inner-ring housing members being to slide through the rolling element;
 the outer-ring holder having a grooved opening supporting the outer-ring housing member of the bearing;
 the inner-ring holder having a grooved opening supporting the inner-ring housing member of the bearing;
 at least one of the outer-ring and inner-ring housing members being vertically divided into two parts;
 the grooved opening of the outer-ring holder or the inner-ring holder on a side of the two-divided housing member having a dimension smaller than a vertical dimension of the two-divided housing member with which the rolling element is in contact with the two-divided housing member.

2. An X-ray diagnostic apparatus according to claim 1, wherein a difference between a vertical dimension of the housing member and a dimension of the grooved opening is set within a limit of elasticity of the rolling element.

3. An X-ray diagnostic apparatus according to claim 1, wherein the support mechanism is a column having the outer-ring holder or the inner-ring holder and supporting the arm.

4. An X-ray diagnostic apparatus according to claim 1, wherein the support mechanism is a floor arm in an arm form having any of the outer-ring holder or the inner-ring holder and having, at one end, a center of horizontal rotation.

5. An X-ray diagnostic apparatus comprising:
 a support mechanism that supports an arm provided with an X-ray tube at one end and an imager at the other end; and
 a rotary mechanism that makes the support mechanism rotatable;
 the rotary mechanism including a bearing;
 the bearing including a rolling element, an outer-ring housing member and an inner-ring housing member;
 the outer-ring and inner-ring housing members being to slide through the rolling element, and forming a container to receive the rolling element;
 the rolling element being received deformed in the container.

6. An X-ray diagnostic apparatus according to claim 5, wherein the rolling element is set to deform within a limit of elasticity of the rolling element.

7. An X-ray diagnostic apparatus according to claim 5, wherein the support mechanism is a column fixed on the outer-ring housing member or the inner-ring housing member and supporting the arm.

8. An X-ray diagnostic apparatus according to claim 5, wherein the support mechanism is a floor arm in an arm form fixed on the outer-ring housing member or the inner-ring housing member and having, at one end, a center of horizontal rotation.

9. A rotary mechanism, comprising:
 a bearing;
 an outer-ring holder; and
 an inner-ring holder,
 the bearing including a rolling element, an outer-ring housing member, and an inner-ring housing member, the outer-ring and inner-ring housing members being configured to slide through the rolling element;
 the outer-ring holder having a grooved opening supporting the outer-ring housing member of the bearing;
 the inner-ring holder having a grooved opening supporting the inner-ring housing member of the bearing;
 at least one of the outer-ring and inner-ring housing members being vertically divided into two parts; and
 the grooved opening of the outer-ring holder or the inner-ring holder on a side of the two-divided housing member having a dimension smaller than a vertical dimension of the two-divided housing member with which the rolling element is in contact with the two-divided housing member.

10. The rotary mechanism according to claim 9, wherein, when received in a width smaller than a dimension provided by a thickness of the two-divided housing member and the gap, the rolling element is to configured deform by a difference of dimension.

11. The rotary mechanism according to claim 9, wherein the rolling element is configured to deform within a limit of elasticity of the rolling element.

12. The rotary mechanism according to claim 9, wherein a raceway of the outer-ring housing member is structured by two surfaces orthogonal in a section taken thicknesswise thereof, a raceway of the inner-ring housing member being structured by two surfaces orthogonal in a section taken thicknesswise thereof, the respective surfaces being opposed to the respective ones of the orthogonal two surfaces structuring the raceway of the outer-ring housing member, wherein the outer-ring housing member or the inner-ring housing member has the orthogonal two surfaces as divided ones.

* * * * *